United States Patent

Schmailzl et al.

[11] Patent Number: 5,169,925
[45] Date of Patent: Dec. 8, 1992

[54] POLYMERIC POLYALKYL-1-OXA-DIAZASPIRODECANES

[75] Inventors: Georg Schmailzl, Gersthofen; Gerhard Pfahler, Augsburg; Günther Nowy, Aystetten, all of Fed. Rep. of Germany

[73] Assignee: Hoechst Aktiengesellschaft, Frankfurt am Main, Fed. Rep. of Germany

[21] Appl. No.: 538,111

[22] Filed: Jun. 14, 1990

[30] Foreign Application Priority Data

Jun. 16, 1989 [DE] Fed. Rep. of Germany ....... 3919691

[51] Int. Cl.$^5$ .................... C08G 65/22; C08K 5/35; C07D 471/10; C08L 23/12
[52] U.S. Cl. ..................... 528/367; 524/95; 524/99; 524/102; 525/187; 546/18; 546/19
[58] Field of Search ............ 524/95, 99, 102; 528/367; 546/18, 19; 525/187

[56] References Cited

U.S. PATENT DOCUMENTS 4,340,534 7/1982 Wiezer et al. ................ 524/99

Primary Examiner—John Kight, III
Assistant Examiner—Shelley A. Wright
Attorney, Agent, or Firm—Connolly & Hutz

[57] ABSTRACT

Novel polymeric polyalkyl-1-oxa-diazaspirodecanes of the formula I

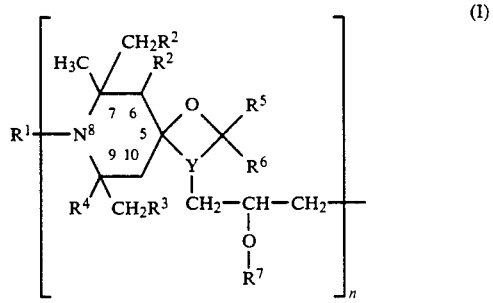

are very effective stabilizers for natural any synthetic polymers. They have very low volatility, high migration resistance and high thermal stability.

11 Claims, No Drawings

POLYMERIC POLYALKYL-1-OXA-DIAZASPIRODECANES

The invention relates to novel polyalkyl-1-oxa-diazaspirodecanes and their use as light stabilizers for the stabilization of organic polymers against photooxidation.

High molecular weight polyalkylpiperidine stabilizers are known, for instance the condensation product of N-$\beta$-hydroxyethyl-2,2,6,6-tetramethyl-4-hydroxypiperidine with succinic acid (cf. U.S. Pat. No. 4,232,131). This compound is commercially available. Although it is very effective, it is not satisfactory in all respects.

Novel, highly effective light stabilizers have now been found which are polymeric polyalkyl-1-oxa-diazaspirodecane compounds.

The present invention accordingly provides polymeric polyalkyl-1-oxa-diazaspirodecanes of the formula I

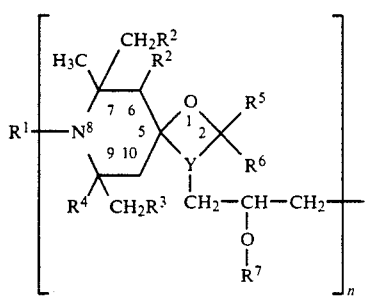

in which
n is an integer from 2 to 50,
Y is a group of the formula II or III,

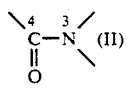 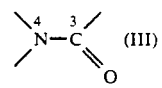

the indices 3 and 4 giving the ring positions in the diazaspirodecane system and one bond of the nitrogen being linked with a $CH_2$ group of the propylene-2-oxy group, $R^1$ a hydrogen atom, an oxygen atom, an NO group, a $C_1$-$C_{12}$-alkyl group, an allyl group, a $C_1$-$C_{22}$-acyl group, or a benzyl group, $R^2$ and $R^3$ are either identical and are a hydrogen atom or are a $C_1$-$C_5$-alkyl group, $R^4$ then being a methyl group, or $R^2$ is a hydrogen atom or a $C_1$-$C_5$-alkyl group and $R^3$ and $R^4$, together with the carbon atoms linking them, form a $C_5$- or $C_8$-cycloalkyl group or a group of the formula

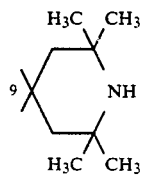

$R^5$ and $R^6$ are identical or different and represent a hydrogen atom, a $C_1$-$C_{30}$-alkyl group, represent an unsubstituted or chlorine- or $C_1$-$C_4$-alkyl-substituted phenyl or naphthyl group or represent an unsubstituted or $C_1$-$C_4$-alkyl-substituted $C_7$-$C_{12}$-phenylalkyl group, or $R^5$ and $R^6$, together with the carbon atom linking them, form an unsubstituted or mono- to tetra-$C_1$-$C_4$-alkyl substituted $C_5$-$C_{18}$-cyclolkyl group or a group of the formula

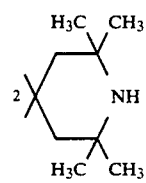

and $R^7$ is a hydrogen atom or a $C_1$-$C_{22}$-acyl group, or $R^7$, in the terminal monomer unit, has no meaning so that the oxygen atom is linked with the terminal $CH_2$ group and forms an oxirane ring.

The novel compounds conform to the formula I

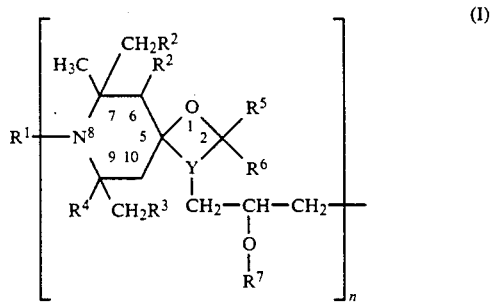

in which
n is an integer from 2 to 50, preferably 2 to 20 and, in particular, 2 to 10,
Y is a group of the formula II or III,

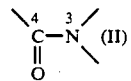 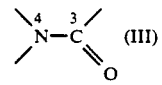

the indices 3 and 4 giving the ring positions in the diazaspirodecane system and one bond of the nitrogen being linked with a $CH_2$ group of the propylene-2-oxy group, $R^1$ is a hydrogen atom, an oxygen atom, an NO group, a $C_1$-$C_{12}$-alkyl group, preferably $C_1$-$C_4$-alkyl group, an allyl group, a $C_1$-$C_{22}$-acyl group, preferably acetyl, or a benzyl group. In particular, $R^1$ is a hydrogen atom.

$R^2$ and $R^3$ are either identical and are a hydrogen atom or are a $C_1$-$C_5$-alkyl group, preferably hydrogen, $R^4$ then being a methyl group, or $R^2$ is a hydrogen atom or a $C_1$-$C_5$-alkyl group and $R^3$ and $R^4$, together with the carbon atoms linking them, form a $C_5$- or $C_6$-cycloalkyl group or a group of the formula

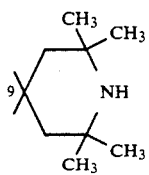

$R^5$ and $R^6$ are identical or different and represent a hydrogen atom, a $C_1$–$C_{30}$-, preferably $C_1$–$C_{18}$-, and in particular $C_1$–$C_5$-alkyl group, represent an unsubstituted or chlorine- or $C_1$–$C_4$-alkyl-substituted phenyl or naphthyl group, preferably a phenyl group, or represent an unsubstituted or $C_1$–$C_4$-alkyl-substituted $C_7$–$C_{12}$-phenylalkyl group, preferably a benzyl group.

Otherwise $R^5$ and $R^6$, together with the carbon atom linking them, form an unsubstituted or mono- to tetra-$C_1$–$C_4$-alkyl-substituted, preferably -methyl-substituted, $C_5$–$C_{18}$-, preferably $C_5$–$C_{12}$-cycloalkyl group or a group of the formula

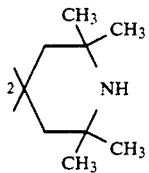

$R^7$ is hydrogen atom, a $C_1$–$C_{22}$-acyl group, preferably a hydrogen atom or an acetyl group and, in particular, a hydrogen atom, or $R^7$, in the terminal monomer unit, has no meaning so that the oxygen atom is linked to the terminal $CH_2$ group and forms an oxirane ring.

Examples of the monomer starting materials (VI) from which the oligomers and according to the invention of the formula I ca prepared are:

(1) 2,2,7,7,9,9-Hexamethyl-3-(2,3-epoxypropyl) -1-oxa-3,8-diaza-4-oxo-spiro-[4,5]-decane (2) 2,2,7,7,9,9-Hexamethyl-4-(2,3-epoxypropy) -1-oxa-3-oxo-4,8-diaza-spiro-[4,5]-decane (3) 2,2,4,4,10,10,12,12-Octamethyl-7-oxa -3,11,14-triazaa-14-(2,3-epoxypropyl)-15-oxo-dispiro-[5.1.5.2]-pentadecane (4) 2,7,7,9,9-Pentamethyl-2-octadecyl-3-(2,3-epoxypropyl)-1-oxa-3,8-diaza-4-oxo-spiro-[4.5]-decane (5) 2,7,7,9,9-Pentamethyl-2-benzyl -3-(2,3-epoxypropyl)-1-oxa-3,8-diaza -4-oxo-spiro-[4.5]-decane (6) 7,7,9,9-Tetramethyl-2,2-diheptyl -3-(2,3-epoxypropyl)1-oxa-3,8-diaza -4-oxo-spiro-[4.5]-decane (7) 7,7,9,9-Tetramethyl-2,2-dibenzyl -3-(2,3-epoxypropyl-1-oxa-3,8-diaza 4-oxo-spiro-[4.5]-decane (8) 7,7,9,9-Tetramethyl-2-methyl-3-(2,3-epoxypropyl)-1-oxa-3,8-diaza-4-oxo-spiro-[4.5]-decane (9) 7,7,9,9-Tetramethyl-2-iso-nonyl-3-(2,3-epoxypropy)-1-oxa-3,8-diaza-4-oxo -spiro-[4.5]-decane

(10) 2,2,4,4-Tetramethyl-7-oxa-3,14-diaza -14-(2,3-epoxypropyl)-15-oxo-dispiro-[5.1.5.2]-pentadecane

(11) 2,2,4,4-Tetramethyl-7-oxa-3,20-diaza-20-(2,3-epoxypropyl)-21-oxo-dispiro-[5.1.11.2]-heneicosane

(12) 2,7,7,9,9-Pentamethyl-2-undecyl-1-oxa-3-oxo-4-(2,3-epoxypro-pyl)-4,8-diaza-spiro-[4.5]-decane

(13) 7,7,9,9-Tetramethyl-2-ethyl-1-oxa -3-oxo-4-(2,3epoxypropyl)-4,8-diaza-spiro -[4.5]-decane

(14) 7,7,9,9-Tetraamethyl-2-iso-heptyl-1-oxa -3-oxo-4-(2,3-epoxypropy-1)-4,8-diaza -spiro-[4.5]-decane

(15) 2,2,4,4-Tetramethyl-7-oxa-3,15-diaza -(2,3-epoxypropyl)-14-oxo-dispiro-5.1.5.2]-pentadecane and also salts of these compounds with protonic acids.

The monomers (VI) for the -preparation of the novel compounds are obtained by nucleophilic substitution of the halogen atom in the epihalohydrin of the formula V, Hal being understood to mean a chlorine, bromine or iodine atom, preferably chlorine, by polyalkyloxadiazaspirodecanes of the formula IV or salts thereof with protonic acids according to the following reaction scheme with the elimination of hydrogen halide. Heating of the oxirane then leads to the formation of the oligomers and polymers according to the invention of the formula I

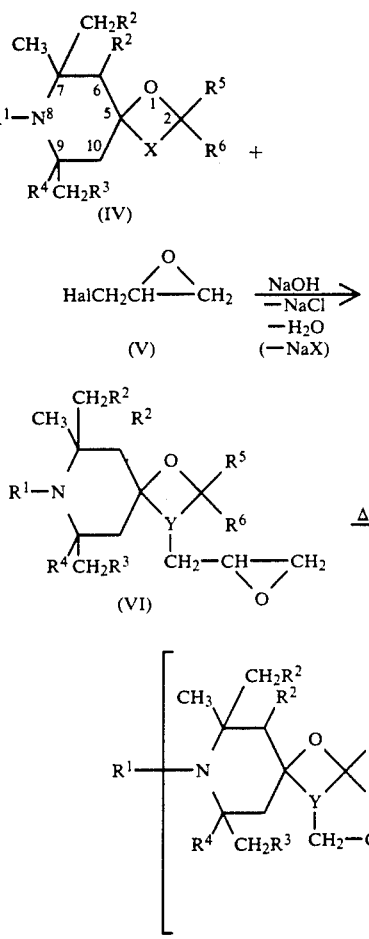

In the formulae of the reaction scheme, the radicals $R^2$, $R^3$, $R^4$, $R^5$, $R^6$, Y, Hal and n have the meanings given above: the radical $R^1$ is hydrogen and the radical $R^7$ is likewise hydrogen or, in the terminal monomer unit, has no meaning so that the oxygen atom forms an oxirane ring with the terminal $CH_2$ group.

The compounds VI are synthesized by reacting the starting materials (IV) and (V) in the molar ratio of 1:1 to 1:5, preferably 1:1 to 1:2, and particularly 1:1 to 1:1.2, in an inert organic solvent in the presence of an equal to twenty-fold molar amount of solid alkali metal hydroxide or the corresponding amount of a 20 to 50% strength aqueous solution thereof, with the use of a phase transfer catalyst. The reaction temperature is from 20 to 120, preferably 20 to 80 and in particular 40° to 60° C.

Suitable organic solvents are aliphatic or aromatic hydrocarbons such as, for example, petroleum ether, hexane, heptane, naphtha fractions, toluene, cyclohexane, xylene etc.

Phase transfer catalysts are understood to mean substances from the group comprising quaternary ammonium and phosphonium halides. Also very suitable are polyethylene glycols and dialkyl ethers of polyethylene glycols. The amount required is 0.1 to 5% by weight, relative to compound (IV).

Generally, the reaction is complete after one to 20 hours.

The compounds VI are isolated by separating the phases, optionally after adding a little water. The organic phase is washed several times with water, dried over a desiccant such as $Na_2SO_4$ or $MgSO_4$ and concentrated. This usually gives oily products.

Heating the epoxides which have been obtained in this manner to 100 to 240, preferably 100 to 200 and in particular 120° to 180° C., gives solid, amorphous, initially glassy polymers for which $2 \leq n \leq 50$. Short polymerization periods give low degrees of polymerization and long polymerization periods give high degrees of polymerization. Similarly, a tendency towards higher degrees of polymerization is observed with increasing temperature.

The polymers or oligomers can also prepared by not initially isolating the epoxides but by bringing the entire reaction mixture, after reacting the epichlorohydrin with the azaspirodecane, to the abovementioned higher temperatures and, after polymerization is complete, working up the reaction mixture.

After polymerization, the terminal secondary amine function of the polymer can, if desired, be converted by methods known per s to give derivatives.

The polyalkyloxadiazaspirodecanes used as starting materials are known and can be obtained according to the directions given in U.S. Pat. No. 4,110,334 and U.S. Pat. No.4,107,139.

The compounds according to the invention are used as light stabilizers in organic polymers, for example in those listed below:

1. Polymers of mono- and di-olefins, for example polyethylene (which may optionally have been crosslinked), polypropylene, polyisobutylene, poly-1-butene, polymethyl-1-pentene, polyisoprene or polybutadiene and also polymers of cycloolefins such as, for example, of cyclopentene or norbornene.

2. Mixtures of the polymers listed under 1), for example mixtures of polypropylene with polyethylene or with polyisobutylene.

3. Copolymers of mono- and di-olefins, one with another or with other vinyl monomers, such as, for example, ethylene-propylene copolymers, propylene-but-1-ene copolymers, propylene-isobutylene copolymers, ethylenebut -1-ene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers and salts thereof (ionomers), and also terpolymers of ethylene with propylene and a diene such as hexadiene, dicyclopentadiene or ethylidenenorbornene.

4. Polystyrene.

5. Copolymers of styrene or α-methylstyrene with dienes or acryloyl derivatives, such as, for example, styrenebutadiene, styrene-maleic anhydride, styrene-acrylonitrile, styrene-ethyl methacrylate, styrene-butadieneethyl acrylate, styrene-acrylonitrile-methyl acrylate; highly impact-resistant mixtures made from styrene copolymers and another polymer such as, for example, a polyacrylate, a diene polymer or an ethylene-propylenediene terpolymer; also, block copolymers of styrene such as, for example, styrene-butadiene-styrene, styrene isoprene-styrene, styrene-ethylene/butylene-styrene or styrene-ethylene/propylene-styrene.

6. Graft copolymers of styrene such as, for example, styrene onto polybutadiene, styrene and acrylonitrile onto polybutadiene, styrene and maleic anhydride onto polybutadiene, styrene and alkyl acrylates or alkyl methacrylates onto polybutadiene, styrene and acrylonitrile onto ethylene-propylene-diene terpolymers, styrene and acrylonitrile onto polyalkyl acrylates or polyalkyl methacrylates, styrene and acrylonitrile onto acrylate-butadiene copolymers, and also mixtures thereof with the copolymers listed under 5) such as are known, for example, as ABS, MBS, ASA or AES polymers.

7. Halogen-containing polymers such as, for example, polychloroprene, chlorinated rubber, chlorinated or chlorosulfonated polyethylene, epichlorohydrin-homo- and -copolymers, in particular polymers made from halogen containing vinyl compounds such as, for example, polyvinyl chloride, polyvinylidene chloride, polyvinyl fluoride and polyvinylidene fluoride; also copolymers thereof such as vinyl chloride-vinylidene chloride, vinyl chloride-vinyl acetate or vinylidene chloride-vinyl acetate.

8. Polymers which are derived from $\alpha,\beta$-unsaturated acids and derivatives thereof, such as polyacrylates and polymethacrylates, polyacrylamides and polyacrylonitriles.

9. Copolymers of the monomers listed under 8), one with another or with other unsaturated monomers, such as, for example, acrylonitrile-butadiene copolymers, acrylonitrile -alkyl acrylate copolymers, acrylonitrile-alkoxyacrylate copolymers, acrylonitrile-vinyl halide copolymers or acrylonitrile-alkyl methacrylate-butadiene terpolymers.

10. Polymers which are derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinyl butyral, polyallyl phthalate, and polyallylmelamine.

11. Homopolymers and copolymers of cyclic ethers, such as polyethylene glycols, polyethylene oxide, polypropylene oxide or copolymers thereof with bisglycidyl ethers.

12. Polyacetals such as polyoxymethylene and also those polyoxymethylenes which contain comonomers such as, for example, ethylene oxide.

13. Polyphenylene oxides and polyphenylene sulfides.

14. Polyurethanes which are, on the one hand, derived from polyethers, polyesters and polybutadienes having terminal hydroxyl groups and on the other hand from aliphatic or aromatic polyisocyanates, and also the precursors thereof (polyisocyanates-polyols prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethyleneterephthalamide, poly-m-phenylene-isophthalamide, and also copolymers thereof with polyethers such as, for example, with polyethylene glycol, polypropylene glycol or polytetramethylene glycol.

16. Polyureas, polyimides and polyamide-imides.

17. Polyesters which are derived from dicarboxylic acids and diols and/or from hydroxycarboxylic acids or from the corresponding lactones, such as polyethylene terephthalate, polybutylene terephthalate, poly-1,4-dimethylolcyclohexane terephthalate, poly(2,2-bis(4-hydroxyphenyl) -propane) terephthalate, polyhydroxybenzoates, and also block-polyether-esters which are derived from polyethylene having hydroxyl terminal groups, dialcohols and dicarboxylic acids.

18. Polycarbonates.

19. Polysulfones and polyether sulfones.

20. Crosslinked polymers which are derived from aldehydes, on the one hand, and phenols, urea or melamine on the other hand, such as phenol-formaldehyde resins, urea-formaldehyde resins and melamine-formaldehyde resins.

21. Drying and non-drying alkyd resins.

22. Unsaturated polyester resins which are derived from copolyesters of saturated and unsaturated dicarboxylic acids with polyhydric alcohols and also from vinyl compounds as crosslinking agents, and also the halogen containing flame-retardant modifications thereof.

23. Crosslinkable acrylic resins which are derived from substituted acrylic esters, such as, for example, from epoxyacrylates, urethane-acrylates or polyesteracrylates.

24. Alkyd resins, polyester resins and acrylate resins, which have been crosslinked with melamine resins, urea resins, polyisocyanates or epoxy resins.

25. Crosslinked epoxy resins which are derived from polyepoxides, for example from bis-glycidyl ethers or from cycloaliphatic diepoxides.

26. Natural polymers such as cellulose, natural rubber, gelatines and also the polymer-homologous chemically converted derivatives thereof such as cellulose acetates, cellulose propionates, and cellulose butyrates, and the cellulose ethers such as methylcellulose.

27. Mixtures of the abovementioned polymers such as, for example, PP/EPDM, polyamide 6/EPDM or ABS, PVC/EVA, PVC/ABS, PVC/MBS, PC/ABS, PBTP/ABS, PC/ASA, PC/PBT, PVC/CPE, PVD/acrylate, POM/thermoplastic PU, POM/acrylate, POM/MBS, PPE/HIPS, PPE/polyamide 6.6 and copolymers, PA/HDPE, PA/PP and PA/PPE.

28. Naturally occurring and synthetic organic substances which are pure monomers or mixtures of monomers such as, for example, mineral oils, animal and vegetable fats, oils and waxes, or oils, fats and waxes based on synthetic esters or mixtures of these substances.

29. Aqueous dispersions of natural or synthetic rubber.

The novel stabilizers are generally incorporated by customary methods into organic polymers. The incorporation can, for example, be carried out by admixing the compounds and optionally other additives with the melt before or during shaping. The incorporation can also be carried out by introducing the dissolved or dispersed compounds directly into the polymer or by admixing these compounds with a solution, suspension or emulsion of the polymer, optionally with subsequent evaporation of the solvent. The amount to added to the polymers is from 1.0% by weight, relative to the material to be stabilized.

The novel compounds can also be added to the polymers which are to be stabilized in the form of a masterbatch which contains these compounds, for example, in a concentration of 2.5 to 50, preferably 5.0 to 20% by weight.

In addition, the organic polymers which are to be stabilized may contain other antioxidants of the type given below, such as for example:

1. Alkylated monophenols, for example
2,6-di-t-butyl-4-methylphenol, 2-t-butyl-4,6-dimethylphenol, 2,6-di-t-butyl-4-ethylphenol, 2,6-di-t-butyl-4-n-butylphenol, 2,6-di-t-butyl-4-i-butylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-t-butyl-4-methoxymethylphenol.

2. Alkylated hydroquinones, for example
2,6-di-t-butyl-4-methoxyphenol, 2,5-di-t-butyl-hydroquinone, 2,5-di-t-amyl-hydroquinone, 2,6-diphenyl-4-octadecyloxyp-henol.

3. Hygroxylated thiodiphenyl ethers, for example
2,2'-thio-bis-(6-t-butyl-4-methylphenol), 2,2'-thio-bis(4-octylphenol), 4,4'-thio-bis-(6-t-butyl-3-ethylphenol), 4,4'-thio-bis-(6-t-butyl-2-ethylphenol).

4. Alkylidene-bisphenols, for example
2,2'-methylene-bis-(6-t-butyl-4-methylphenol), 2,2'-methylene-bis-(6-t-butyl-4-ethylphenol), 2,2'-methylene-bis-[(4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-t-butylphenol), 2,2'-ethylidene-bis-(4,6-di-t-butylphenol), 2,2'-ethylidene-bis-(6-t-butyl-4-isobutylphenol), 2,2'-methylene-bis-[6-(α-methylbenzyl)-4-nonylphenol]2,2'-methylene-bis-[6-(α,α-dimethylbenzyl) -4-nonylphenol], 4,4'-methylene-bis-(2,6-di-t-butylphenol), 4,4'-methylene-bis(6-t-butyl-2-methylphenol), 1,1-bis-(5-t-butyl-4-hydroxy-2-methylphenyl)-butane, 2,6-di-(3-t-butyl-5-methyl-2-hydroxybenzyl)-4methylphenol, 1,1,3-tris-(5-t-butyl-4-hydroxy-2-methylphenyl)butane, 1,1-bis-(5-t-butyl-4-hydroxy-2-methylphenyl) -3-n-dodecylmercaptobutane, di-(3-t-butyl-4-hydroxy-5-methylphenyl)-dicyclopentadiene, di-[2-(3'-t-butyl-2'-hydroxy-5'-methyl-benzyl) -6-t-butyl-4-methyl-phenyl] terephthalate, ethylene glycol-bis-[3,3-bis(3'-t-butyl-4'-hydroxyphenyl) butyrate].

5. Benzyl compounds, for example
1,3,5-tri-(3,5-di-t-butyl-4-hy-droxybenzyl) -2,4,6-trimethylbenzene, di-(3,5-di-t-butyl-4-hydroxybenzyl) sulfide, isooctyl 3,5-di-t-butyl-4-hydroxybenzyl-mercaptoacetate, bis-(4-t-butyl-3-hydroxy-2,6-dimethylbenzyl)-dithiol terephthalate, 1,3,5-tris-(3,5-di-t-butyl-4-hydroxybenzyl) isocyanurate, 1,3,5-tris-(4-t-butyl-3-hydroxy-2,6-dimethylbenzyl) isocyanurate, dioctadecyl 3,5-di-t-butyl-4-hydroxybenzyl-phosphonate, calcium salt of mono-ethyl 3,5-di-t-butyl-4-hydroxybenzyl -phosphonate.

6. Acylaminophenols, for example
4-hydroxy-lauranilide, 4-hydroxy-stearanilide, 2,4-bis-octylmercapto-6-(3,5-di-t-butyl-4-hydroxyanilino)-s-triazine, octyl N-(3,5-di-t-butyl-4-hydroxyphenyl)-carbamate.

7. Esters of β-(3,5-di-t-butyl-4-hydroxyphenyl) -propionic acid with mono- or poly-hydric alcohols, such as, for example, with

| | |
|---|---|
| methanol, | diethylene glycol, |
| octadecanol, | triethylene glycol, |
| 1,6-hexanediol, | pentaerythritol, |
| neopentyl glycol, | tris-hydroxyethyl isocyanurate, |
| thiodiethylene glycol | di-hydroxyethyl oxamide. |

8. Esters of β-(5-t-butyl-4-hydroxy-3-methylphenyl)-propionic acid with mono- or poly-hydric alcohols, such as, for example, with

| | |
|---|---|
| methanol, | diethylene glycol, |
| octadecanol, | triethylene glycol, |
| 1,6-hexanediol, | pentaerythritol, |
| neopentyl glycol, | tris-hydroxyethyl isocyanurate, |
| thiodiethylene glycol | di-hydroxyethyl-oxamide. |

9. Amides of β-3,5-di-t-butyl-4-hydroxyphenyl) -propionic acid, such as, for example, N,N'-di-(3,5-di-t-butyl-4-hydroxyphenylpropionyl) -hexamethylenediamine, N,N'-di-(3,5-di-t-butyl-4-hydroxyphenylpropionyl) -trimethylenediamine, N,N'-di-(3,5-di-t-butyl-4-hydroxyphenylpropionyl) -hydrazine.

In addition, the polymers to be stabilized may contain further additives such as for example:

1. UV-Absorbers and light stabilizers 1.1 2-(2'-Hydroxyphenyl)-benzotriazoles such as, for example, the 5'-methyl, 3',5'-di-t-butyl, 5'-t-butyl, 5'-(1,1,3,3-tetramethylbutyl), 5-chloro -3',5'-di-t-butyl, 5-chloro-3'-t-butyl -5'-methyl, 3'-sec-butyl-5'-t-butyl, 4'-octoxy, 3',5'-di-t-amyl, 3',5'-bis-(α,α-dimethylbenzyl) derivative.

1.2 2-Hydroxybenzophenones, for example the 4-hydroxy, 4-methoxy, 4-octoxy, 4-decyloxy, 4-dodecyloxy, 4-benzyloxy, 4,2',4'-trihydroxy, 2'-hydroxy-4,4'-dimethoxy derivative.

1.3 Esters of optionally substituted benzoic acids, for example 4-t-butyl-phenyl salicylate, -phenyl salicylate, octylphenyl salicylate, dibenzoylresorcinol, bis-(4-t-butylbenzoyl)-resorcinol, benzoylresorcinol, 2,4-di-t-butylphenyl 3,5-di-t-butyl-4-hydroxy-benzoate, hexadecyl 3,5-di-t-butyl-4-hydroxybenzoate.

1.4 Acrylates, for example ethyl α-cyano-β,β-diphenyl acrylate and isooctyl α-cyano-β,β-diphenyl acrylate, ethyl α-carbomethoxycinnamate, methyl α-cyano-β-methyl-p-methoxycinnamate and butyl α-cyano-β-methyl-p-methoxycinnamate, methyl α-carbomethoxy-p-methoxycinnamate, and N-(β-carbomethoxy-β-cyano-vinyl)-2-methylindoline.

1.5 Nickel compounds, for example nickel complexes of 2,2'-thio-bis-[4-(1,1,3,3-tetramethylbutyl)phenol] such as the 1:1- or 1:2-complex, optionally with additional ligands such as n-butylamine, triethanolamine or N-cyclohexyldiethanolamine, alkylnickel dithiocarbamates, nickel salts of monoalkyl 4-hydroxy-3,5-di-t-butyl-benzylphosphonates such as those of the methyl or ethyl esters, nickel complexes of ketoximes such as those of 2-hydroxy-4-methylphenyl undecyl ketoxime, nickel complexes of 1-phenyl-4-lauroyl-5-hydroxypyrazole, optionally with additional ligands, and nickel salts of 2-hydroxy-4-alkoxybenzophenones. 1.6 Sterically hindered amines, for example 1.6.1, bis-(2,2,6,6-tetramethylpiperidyl) sebacate, bis-(1,2,2,6,6-pentamethylpiperidyl) sebacate, bis-(2,2,6,6-tetramethylpiperidyl) glutarate, bis-(1,2,2,6,6-pentamethylpiperidyl) glutarate, bis-(2,2,6,6-tetramethylpiperidyl) succinate, bis-(1,2,2,6,6-pentamethylpiperidyl) succinate, 4-stearyloxy-2,2,6,6-tetramethylpiperidine, 4-stearyloxy-1,2,2,6,6-pentamethylpiperidine, 4-stearoyloxy-2,2,6,6-tetramethylpiperidine, 4-stearoyloxy-1,2,2,6,6-pentamethylpiperidine, 2,2,6,6-tetramethylpiperidyl behenate, 1,2,2,6,6-pentamethylpiperidyl behenate, 2,2,4,4-tetramethyl-7-oxa-3,20-diazadispiro [5.1.11.2]-heneicosan-21-one, 2,2,3,4,4-penta-methyl-7-oxa-3,20-diaza-dispiro 5.1.11.2]-heneicosan-21-one, 2,2,4,4-tetramethyl-3--acetyl-7-oxa-3,20-diaza-dispiro-5.1.11.2]-heneicosan-21-one, 2,2,4,4-tetramethyl-7-oxa-3,20-diaza-20-(β-lauryloxycarbonylethyl)-21-oxo-dispiro -5.1.11.2]-heneicosane, 2,2,3,4,4-pentamethyl-7- oxa-3,20-diaza-20-(β-lauryloxycarbonylethyl)-21-oxo-dispiro-[5.1.11.2]- heneicosane, 2,2,4,4-tetramethyl-3-acetyl-7-oxa-3,20-diaza -20-(β-lauryloxycarbonylethyl)-21-oxo-dispiro -[5.1.11.2]-heneicosane, 1,1'-3,3',5,5'-hexahydro -2,2',4,4',6,6'-hexaaza-2,2',6,6'-bismethano-7,8-dioxo-4,4'-bis-(1,2,2,6,6-pentamethyl-4-piperidyl)-biphenyl, NN'N''N'''-tetrakis-{2,4-bis-[N(-2,2,6,6-tetramethyl -4-piperidyl)butylamino]1,3,5-triazin-6-yl}-4,7-diazadecane-1,10-diamine, NN'N''N'''-tetrakis-{2,4-bis-[N-(1,2,2,6,6-pentamethyl-4-piperidyl)-butylamino]-1,3,5-triazin -6-yl}-4,7-diazadecane-1,10-diamine, NN'N''N'''-tetrakis-{2,4-bis-[N-(2,2,6,6-tetramethyl -4-piperidyl)-methoxypropylamino]-1,3,5-triazin-6-yl}-4,7-diazadecane-1,10-diamine, NN'N''N'''-tetra-kis-{2,4-bis-[N-(1,2,2,6,6-pentamethyl-4-piperidyl)-methoxypropylamino]-1,3,5-triazin-6-yl}-4,7-diazadecane-1,10-diamine, bis-(1,2,2,6,6-pentamethylpiperidyl)-n-butyl-3,5-di-tert-butyl-4-hydroxybenzyl malonate, tris-(2,2,6,6-tetramethyl -4-piperidyl) nitrilotriacetate, tetrakis -(2,2,6,6-tetramethyl-4-piperidyl) -1,2,3,4-butanetetracarboxylic acid, 1,1'-(1,2-ethanediyl)-bis -(3,3,5,5-tetramethyl-piperazinone).

1.6.2. Poly-N,N'-bis-(2,2,6,6-tetramethyl-4-piperidyl)-1,8-diazadecylene, the condensation product of 1-(2-hydroxyethyl)-2,2,6,6-tetraethyl-4-hydroxypiperidine and succinic acid, the condensation product of N,N'-bis-(2,2,6,6-tetramethyl -4-piperidyl)-hexamethylenediamine and 4-tertoctylamino -2,6-dichloro-1,3,5-triazine, the condensation product of N,N'-bis-(2,2,6,6-tetramethyl -4-piperidyl)-hexamethylenediamine and 4-morpholino-2,6-dichloro-1,3,5-triazine.

In many cases, a combination of the compounds according to the invention with the compounds listed under 1.6.1 proves to be particularly advantageous.

1.7 Oxamides, for example 4,4'-di-octyloxy-oxanilide, 2,2'-di-octyloxy-5,5'-di-t-butyl-oxanilide, 2,2'-didodecyloxy-5,5'-di-t-butyloxanilide, 2-ethoxy-2'-ethyl-oxanilide, N,N'-bis-(3-dimethylaminopropyl)-oxamide, 2-ethoxy-5-t-butyl-2'-ethyloxanilide and the mixture thereof with 2-ethoxy-2'-ethyl-5,4-di-t-butyl-oxanilide, mixtures of ortho- and para-methoxy- and of o- and p-ethoxy di-substituted oxanilides.

2. Metal deactivators, for example

N,N'-diphenyloxamide, N-salicylal-N'-salicyloylhydrazine, N,N'-bis-salicyloyl-hydrazine, N,N'-bis-(3,5-di-t-butyl-4-hydro-xyphenyl-propionyl)-hydrazine, 3-salicyloyl-amino-1,2,3-triazole, bis-benzylideneoxalic dihydrazide.

3. Phosphites and phosphonites, for example triphenyl phosphite, diphenyl alkyl phosphites, phenyl dialkyl phosphites, trisnonylphenyl phosphite, trilauryl phosphite, trioctadecyl phosphite, distearyl pentaerythrityl diphosphite, tris(2,4-di-t-butylphenyl) phosphite, diisodecyl pentaerythrityl diphosphite, bis(2,4-di-t-butylphenyl) pentaerythrityl diphosphite, tristearyl sorbityl triphosphite, tetrakis-(2,4-di-t-butylphenyl)-4,4′-biphenylenediphosphonite, 3,9-bis-(2,4-di-t-butylphenoxy) -2,4,8,10-tetraoxa-3,9-diphosphaspiro[5.5]undecane, tris(2-t-butyl-4-thio(2′-methenyl-4′-hydroxy-5′-t-butyl)-phenyl-5-methenyl)-phenyl phosphite.

4. Peroxide-destroying compounds, for example esters of β-thio-dipropionic acid, for example the lauryl, stearyl, ristyl or tridecyl esters, mercaptobenzimidazole, the zinc salt of 2-mercaptobenzimidazole, alkylzinc dithiocarbamates, dioctadecyl sulfide, pentaery-thritol tetrakis-(β-dodecylmercapto) -propionate.

5. Basic co-stabilizers, for example melamine, polyvinylpyrrolidone, dicyandiamide, triallyl cyanurate, urea derivatives, hydrazine derivatives, amines, polyamines, polyurethanes, alkali metal and alkaline earth metal salts of higher fatty acids or phenolates, for example calcium stearate, zinc stearate, magnesium stearate, sodium ricinoleate, potassium palmitate, antimony catecholate or tin catecholate, hydroxides and oxides of alkaline earth metals or of aluminum, for example CaO, MgO, ZnO.

6. Nucleating agents, for example 4-t-butylbenzoic acid, adipic acid, diphenylacetic acid, dibenzylidenesorbitol.

7. Fillers and reinforcing agents, for example calcium carbonate, silicates, glass fibers, asbestos, talc, kaolin, mica, barium sulfate, metal oxides and hydroxides, carbon black, graphite.

8. Other additives, for example plasticizers, lubricants, emulsifiers, pigments, optical brighteners, flame retardants, antistatic agents, blowing agents.

The various additional additives from the abovementioned groups 1 to 6 are added to the polymers which are to be stabilized in an amount from 0.1 to 10, preferably 0.01 to 5% by weight, relative to the total weight of the molding composition. The proportion of the additives from groups 7 and 8 is 1 to 80, preferably 10 to 50% by weight, relative to the total molding composition.

The organic polymers which have been stabilized according to the invention can be used in various forms, for example as films, fibers, tapes, profiles or as binders for paints, adhesives or putties. The prior art polymeric stabilizers have the deficiency that they do not satisfy the industrial requirements in all of the important use parameters, which include not only efficiency but also volatility, migration resistance (equivalent to low leachability) and thermal stability. In contrast, the novel stabilizers according to the invention eminently satisfy these requirements. They are very effective stabilizers and are substantially free from disadvantages which are based on physical properties.

The subject-matter of the invention is further explained with the aid of the examples which follow.

EXAMPLE 1

2,2,7,7,9,9-Hexamethyl-1-oxa-3-(2,3-

-epoxypropyl)-3,8-diaza-4-oxo-spiro-[4.5]

-decane and the oligomer obtained therefrom

To 150 cm$^3$ of toluene were added, in succession, 24.0 g (0.1 mol) of 2,2,7,7,9,9-hexamethyl-1-oxa-3,8-diaza -4-oxo-spiro-[4.5]-decane, 18.5 g (0.2 mol) of epichlorohydrin, 5 drops of tricaprylmethylammonium chloride ((R)Aliquat 336 from Fluka) and 40 g of 50% strength sodium hydroxide solution (=0.5 mol of NaOH), and then the reaction mixture was stirred at 65° C. for 16 hours. After the stirrer had been switched off, two clear phases formed, which were separated. The organic phase was washed three times with 50 c$^3$ of water, dried over 50 g of sodium sulfate, stirred for 30 min with 1 g of active charcoal at room temperature and filtered. The volatile components were eliminated in vacuo. This gave a colorless oil, which is the epoxy compound given in the heading. This compound was heated at 170° C. for three hours and polymerized under these conditions to give a solid, colorless resin having an m.p. of 130° to 184° C. The viscosity number (determined in accordance with DIN 53 728 at 25° C. from a 1% by weight solution in toluene) was 0.03.

EXAMPLES 2 TO 12

The procedure used in Example 1 was repeated. The Table which follows gives the experimental conditions and data concerning the monomeric and polymeric materials involved in the process. Column 2 ("Compound No.") refers to the list of typical monomeric starting materials in the description on page 5 from which, in each case, also the polyalkyldiazaspirodecane used is obtained.

TABLE 1

| Ex. No. | Cpd. No. | Preparation of the epoxy compound | | M.p. of the epoxy compound (°C.) | Polymerization | | Polymer | |
|---|---|---|---|---|---|---|---|---|
| | | time (h) | temp. (°C.) | | time (h) | temp. (°C.) | m.p. (°C.) | viscosity number[1] |
| 2 | 2 | 15 | 60 | 175 | 6 | 170 | 142–183 | 0.02 |
| 3 | 15 | 13 | 55 | 95–99 | 5 | 170 | 168–229 | 0.02 |
| 4 | 1 | 16 | 65 | oil | 6 | 170 | 151–208 | 0.04 |
| 5 | 3 | 18 | 50 | 165 | 6 | 170 | 55–191 | 0.03 |
| 6 | 5 | 15 | 60 | oil | 6 | 180 | 128–149 | 0.04 |
| 7 | 6 | 14 | 40 | oil | 3 | 150 | 57–94 | 0.03 |
| 8 | 7 | 14 | 60 | oil | 6 | 180 | 144–170 | 0.03 |
| 9 | 10 | 15 | 60 | oil | 3 | 170 | 138–190 | 0.01 |
| 10 | 10 | 15 | 60 | oil | 6 | 170 | 172–247 | 0.03 |
| 11 | 11 | 6 | 50 | 138 | 3 | 170 | 101–163 | 0.02 |
| 12 | 11 | 12 | 60 | oil | 6 | 170 | 129–177 | 0.03 |

[1]determined in accordance with DIN 53 728 (1% by weight in toluene, 25° C.)

The Examples which follow demonstrate the superiority of the novel compounds relative to the prior art.

EXAMPLE 13

To 100.00 parts by weight of polypropylene powder

|     |                                                                                                                                      |
| --- | ------------------------------------------------------------------------------------------------------------------------------------ |
|     | (MFI 230/5: 2–5 g/10 min) was added with stirring a mixture (in acetone) of                                                          |
| 0.20 part by weight of | calcium stearate,                                                                                                         |
| 0.15 part by weight of | glycol bis[3,3-bis-(4'-hydroxy-3'-tert-butyl-phenyl)-butanoate],                                                          |
| 0.05 part by weight of | dioctadecyl disulfide,                                                                                                    |
| 65.00 part by weight of | talc (type OOS from Lussenac) and                                                                                        |
| 0.50 part by weight of | the stabilizer to be tested.                                                                                              |

The solvent was removed in a rotary evaporator and the mixture was extruded using a laboratory extruder (short compression zone screw, screw diameter: 20 mm, length 20 D, nozzle 30 mm in length, 2 mm in diameter; screw speed: 125 rpm). The granules were injection molded on a Windsor injection molding machine type SP 50 to give 60×60×1 mm plates. T-shaped test pieces were punched from these plates.

The heat aging resistance was determined by suspending these test pieces in a motor-driven frame having rotating trays, within a circulating air drying oven, and subjecting the test pieces to heat stress at 140° C. with a steady supply of fresh air.

The period after which incipient local embrittlement occurred at some points, this being characterized according to DIN 53 383 by the formation of discolored, cloudy, sometimes crumbly patches, was recorded.

The results are given in Table 2.

TABLE 2

| Stabilizer according to Example | Incipient embrittlement after . . . days |
| --- | --- |
| 12 | 87 |
| Comparison A[1] | 65 |

EXAMPLE 14

| To 100.00 parts by weight of | polyethylene powder (MFI 190/2.16: 2–5 g/10 min) was added a solution in acetone of |
| --- | --- |
| 0.2 part by weight of | the stabilizer to be tested. |

This mixture was used, as in Example 13, to prepare 1 mm thick plates.

The heat aging resistance was determined by subjecting these plates to heat stress at 100° C. in a drying oven.

After 4 weeks, the yellowing of the plates was measured in terms of the Yellowness Index in accordance with ASTM D 1925-70 (Hunterlab Colorimeter Model D 25 M-2).

TABLE 3

| Stabilizer according to Example | Yellowness Index (YI) | | |
| --- | --- | --- | --- |
|  | Untreated | After 4 weeks | Change |
| 12 | 19.8 | 22.3 | 2.5 |
| Comparison A | 20.6 | 26.9 | 6.3 |
| Comparison C[2] | 20.4 | 21.3 | 0.9 |

[1] ®Chimasorb 944 according to DE 2,636,144
[2] without any stabilizer to be tested

EXAMPLE 15

| To 100.00 parts by weight of | polyethylene powder (density 0.944 g/cm³ MFI 190/2.16: 0.5 g/10 min) was added a solution in acetone of |
| --- | --- |
| 0.2 part by weight of | the stabilizer to be tested. |

This mixture was used to prepare, as in Example 13, 1 mm thick plates.

The heat aging resistance was determined by treating these plates as in Example 14 and measuring the Yellowness Index, as in Example 14, after 4 weeks.

TABLE 4

| Stabilizer according to Example | Yellowness Index (YI) | | |
| --- | --- | --- | --- |
|  | Untreated | After 4 weeks | Change |
| 12 | 19.9 | 33.9 | 14.0 |
| Comparison A | 29.2 | 87.0 | 57.8 |
| Comparison C | 23.4 | 24.5 | 1.1 |

EXAMPLE 16

| To 100.00 parts by weight of | polypropylene powder (MFI 230/5: 2–5 g/10 min) was added a solution in acetone of |
| --- | --- |
| 0.10 part by weight of | calcium stearate, |
| 0.05 part by weight of | glycol bis-3,3-bis-(4'-hydroxy-3'-tert-butyl-phenyl)butanoate, |
| 0.10 part by weight of | tris-(2,4-di-tert-butyl-phenyl) phosphite and |
| 0.50 part by weight of | the stabilizer to be tested. |

As in Example 13, this mixture was used to prepare granules. These granules were used to prepare 1 mm thick plates as in Example 13.

The light stability was determined by subjecting the samples to long-term irradiation in a "Suntest apparatus" ("Suntest" apparatus supplied by Heraeus POH, UV light filter combination "UV special glass having an IR-reflective coating". Black panel temperature 55° C. ±5° C. No humidification, no rain; exposure distance 32 cm).

The samples were exposed until "pronounced surface embrittlement" was observed (visually).

TABLE 5

| Stabilizer according to Example | Exposure time until pronounced crack formation |
| --- | --- |
| 12 | >3350 h |
| Comparison A | <1632 h |

EXAMPLE 17

The light stability was determined by subjecting the plates which had been prepared in Example 16 to irradiation on revolving specimen holders in an exposure apparatus supplied by Heraeus POH (Xenotest 1200). The radiation intensity was modulated using special filter glass of d=1.7 mm. The light stability was measured in accordance with DIN 53 387 (102 min dry phase, 18 min water spraying, black panel temperature 45° C., humidity 70%). The samples were exposed until there was pronounced surface embrittlement.

TABLE 6

| Stabilizer according to Example | Exposure time until pronounced crack formation |
| --- | --- |
| 12 | 2315 h |
| Comparison A | 1885 h |

EXAMPLE 18

The light stability was determined by processing granules which had been prepared as in Example 16 in a laboratory film blowing apparatus to give 0.1 mm thick films. From these films were punched test pieces according to DIN 53 455, shape 3, reduced in scale in the ratio 1:3.

These test pieces were subjected, under the same conditions as described in Example 17, to irradiation on revolving specimen holders. The exposure time in hours was measured and the elongation at break was determined. The elongation at break was measured on a tensile testing machine using an extension rate of 5 cm/min.

TABLE 7

| Stabilizer according to Example | Exposure time required to give 50% of the original elongation at break |
|---|---|
| 12 | 875 h |
| Comparison A | 625 h |

EXAMPLE 19

| | |
|---|---|
| To 100.00 parts by weight of | polypropylene powder (MFI 230/5: 40–80 g/10 min) was added a solution in acetone of |
| 0.5 part by weight of | pentaerythrityl tetrakis-3-(3,5-di-tert-butyl-4-hydroxyphenyl)propionate, |
| 0.10 part by weight of | tris-(2,4-di-tert-butylphenyl) phosphite and |
| 0.075 part by weight of | the stabilizer to be tested. |

This mixture was used, as in Example 13, to prepare granules.

These granules were used to prepare a 0.1 mm thick film in a laboratory film blowing apparatus. From this film, test pieces of dimensions 50×35 mm were prepared and these were exposed, under the same conditions as described in Example 17, to irradiation on revolving specimen holders. The light stability was determined by measuring the change in the carbonyl number $$= \frac{E(1710\ cm^{-1})}{E(1260\ cm^{-1})}$$

of the exposed samples using an infrared spectrograph in accordance with DIN 53 383/2. A pronounced increase in the carbonyl number indicates relatively high susceptibility to oxidation in the polypropylene and, accordingly, lower stability.

TABLE 8

| Stabilizer according to Example | Increase in the carbonyl number after 840 h |
|---|---|
| 12 | 0.3 |
| Comparison B[3] | 1.6 |

[3] ®Tinuvin 622 according to DE 2,719,131

EXAMPLE 20

| | |
|---|---|
| 100.00 parts by weight of | ethylene-acrylic acid copolymer granules (type ESCN 5110 supplied by Exxon Chemicals) were coated on the surface in a drum mixer with |
| 0.1 part by weight of | a processing stabilizer which is commercially available under the trade name ®Hostanox VP ZnCS 1 and |
| 0.2 part by weight of | the stabilizer to be tested. |

These granules were then extruded in a laboratory extruder to give flat films (thickness 180 μm, width 40 cm). From these films were punched test pieces in accordance with DIn 53 455, shape 3, reduced in scale in the ratio 1:3.

These test pieces were exposed, under the same conditions as described in Example 17, to irradiation on revolving specimen holders. The exposure time in hours and the elongation at break were measured. The elongation at break was determined on a tensile testing machine using an extension rate of 5 cm/min.

TABLE 9

| Stabilizer according to Example | Residual elongation at break after 1800 h of exposure |
|---|---|
| 12 | 50% |
| Comparison A | 30% |

We claim:

1. A polymeric polyalkyl-1-oxa-diazaspirodecane of the formula I $$\left[ R^1 - N^8 \underset{9\ 10}{\overset{7\ 6}{\underset{5}{\bigvee}}} \overset{H_3C}{\underset{R^4}{\bigvee}} \overset{CH_2R^2}{\underset{CH_2R^3}{\bigvee}} \overset{O}{\underset{Y}{\overset{1}{\bigvee}}} \overset{R^5}{\underset{R^6}{\bigvee}} CH_2-\underset{\underset{R^7}{\overset{|}{O}}}{\overset{|}{CH}}-CH_2 \right]_n \quad (I)$$

in which
n is an integer from 2 to 50,
Y is a group of the formula II or III, $$\overset{4}{\underset{\underset{O}{\overset{\|}{C}}}{\bigvee}}\overset{3}{\underset{}{N}}\ (II) \qquad \overset{4}{\underset{}{\bigvee}}\overset{3}{\underset{\underset{O}{\overset{\|}{C}}}{N}}\ (III)$$

the indices 3 and 4 giving the ring positions in the diazaspirodecane system and one bond of the nitrogen being linked with a CH₂ group of the propylene-2-oxy group,
R¹ is a hydrogen atom,
R² and R³ are either identical and are a hydrogen atom or are a C₁–C₅-alkyl group,
R⁴ then being a methyl group, or
R² is a hydrogen atom or a C₁–C₅-alkyl group and R³ and R⁴, together with the carbon atoms linking them, form a C₅- or C₆-cycloalkyl group or a group of the formula

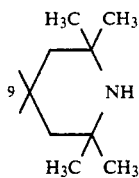

$R^5$ and $R^6$ are identical or different and represent a hydrogen atom, a $C_1$-$C_{30}$-alkyl group, represent an unsubstituted or chlorine- or $C_1$-$C_4$-alkyl-substituted phenyl or naphthyl group or represent an unsubstituted or $C_1$-$C_4$-alkyl-substituted $C_7$-$C_{12}$-phenylalkyl group, or $R^5$ and $R^6$, together with the carbon atom linking them, form an unsubstituted or mono- to tetra-$C_1$-$C_4$-alkyl substituted $C_5$-$C_{18}$-cycloalkyl group or a group of the formula

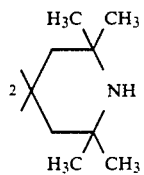

and $R^7$ is a hydrogen atom or a $C_1$-$C_{22}$-acyl group, or $R^7$, in the terminal monomer unit, has no meaning so that the oxygen atom is linked with the terminal $CH_2$ group and forms an oxirane ring.

2. The process as claimed in claim 1, wherein the polymer is a polyolefin.

3. The process as claimed in claim 1, wherein the polymer is a halogen-containing polymer.

4. The process as claimed in claim 1, wherein the polymer is a polyacrylate or polymethacrylate.

5. The process as claimed in claim 1, wherein the polymer is a polystyrene homo- or co-polymer.

6. A process for stabilizing synthetic polymers against the harmful effect of light, which comprises adding to the polymers, optionally in addition to prior art and stabilizing substances, 0.01 to 10 parts by weight, relative to the polymer, of a stabilizer as claimed in claim 1.

7. A synthetic polymer which has been stabilized against UV degradation and which contains 0.01 to 10 parts by weight, relative to the polymer, of a stabilizer as claimed in claim 1.

8. The synthetic polymer as claimed in claim 7, wherein the polymer is a polyolefin.

9. The synthetic polymer as claimed in claim 7, wherein the polymer is a halogen-containing polymer.

10. The synthetic polymer as claimed in claim 7, wherein the polymer is a polyacrylate or polymethacrylate.

11. The synthetic polymer as claimed in claim 7, wherein the polymer is a polystyrene homo- or co-polymer.

* * * * *